(12) United States Patent
Ross

(10) Patent No.: US 9,023,404 B2
(45) Date of Patent: May 5, 2015

(54) FURTHER PREPARATIONS OF SILK PROTEINS, SEED OILS, MONOSACCHARIDE, NATURAL BOTANICALS AND POLYSACCHARIDE MIXTURES IN COMPOSITIONS FOR HAIR CARE OR HAIR REPAIR, AND SKIN CARE AND TOPICAL TREATMENTS

(75) Inventor: Valerie Marie Ross, San Diego, CA (US)

(73) Assignee: Valerie Ross, San Clemente, CA (US)

( * ) Notice: Subject to any disclaimer, the term of this patent is extended or adjusted under 35 U.S.C. 154(b) by 328 days.

(21) Appl. No.: 13/011,902

(22) Filed: Jan. 23, 2011

(65) Prior Publication Data

US 2011/0311655 A1    Dec. 22, 2011

Related U.S. Application Data

(60) Provisional application No. 61/412,023, filed on Nov. 10, 2010, provisional application No. 61/297,685, filed on Jan. 22, 2010.

(51) Int. Cl.

| | |
|---|---|
| A61K 8/97 | (2006.01) |
| A61K 8/60 | (2006.01) |
| A61K 36/185 | (2006.01) |
| A61K 31/715 | (2006.01) |
| A61K 8/34 | (2006.01) |
| A61K 8/36 | (2006.01) |
| A61K 8/44 | (2006.01) |
| A61K 8/73 | (2006.01) |
| A61Q 5/00 | (2006.01) |
| A61Q 7/00 | (2006.01) |
| A61K 9/00 | (2006.01) |
| A61K 9/107 | (2006.01) |

(52) U.S. Cl.
CPC ............. *A61K 31/715* (2013.01); *A61K 8/345* (2013.01); *A61K 8/361* (2013.01); *A61K 8/44* (2013.01); *A61K 8/60* (2013.01); *A61K 8/73* (2013.01); *A61K 8/97* (2013.01); *A61Q 5/002* (2013.01); *A61Q 7/00* (2013.01); *A61K 9/0014* (2013.01); *A61K 9/107* (2013.01)

(58) Field of Classification Search
None
See application file for complete search history.

(56) References Cited

U.S. PATENT DOCUMENTS

| | | | |
|---|---|---|---|
| 2005/0002894 A1* | 1/2005 | Petersohn et al. | 424/74 |
| 2008/0274068 A1* | 11/2008 | Tanaka et al. | 424/60 |

FOREIGN PATENT DOCUMENTS

JP    10310530 A    * 11/1998

* cited by examiner

*Primary Examiner* — Susan Hoffman
(74) *Attorney, Agent, or Firm* — Mintz Levin Cohn Ferris Glovsky and Popeo, P.C.

(57) ABSTRACT

The present invention intends to provide a composition for hair and skin treatment containing a combination consisting of silk amino acid and protein complexes, seed oils, polysaccharides, polyol, monosaccharide, and botanicals. The composition for hair and skin treatment containing the combination consisting of silk amino acid and protein complexes, seed oils, polysaccharides, and botanicals has excellent improvement effects on the condition of the hair follicle and cuticle, imparts moisture to dry hair; thereby reducing the damaging effects of psoriasis, eczema, alopecia, and seborrheic dermatitis. Furthermore, it imparts retention of moisture to the skin resulting in an improved appearance and diminished appearance of lines on the skin. This invention relates to the manufacture of personal care products to be applied to the hair and skin. The compositions may be in the form of hair conditioners, hair growth treatments, shampoos, skin care, skin cleansing, or anti-wrinkle products, and ointments.

20 Claims, No Drawings

FURTHER PREPARATIONS OF SILK PROTEINS, SEED OILS, MONOSACCHARIDE, NATURAL BOTANICALS AND POLYSACCHARIDE MIXTURES IN COMPOSITIONS FOR HAIR CARE OR HAIR REPAIR, AND SKIN CARE AND TOPICAL TREATMENTS

CROSS-REFERENCE TO RELATED APPLICATIONS

This application claims priority under 35 U.S.C. §119(e) to U.S. Provisional Application No. 61/412,023, filed Nov. 10, 2010 and U.S. Provisional Application No. 61/297,685, filed Jan. 22, 2010.

TECHNICAL FIELD AND INDUSTRIAL APPLICABILITY OF INVENTION

The present invention relates to a composition for hair and skin treatment which is characterized by silk amino acid and protein complexes, seed oils, polysaccharides, polyol, monosaccharide, and botanicals.

BACKGROUND ART

The protein structure of the hair is denatured by environmental factors such as uv exposure; physical factors such as heat, friction, and dryness caused by hair dryers, pressing combs, flat-iron straighteners, and so on; and chemical agents such as hair dyes, perms, relaxers, and other hair breaching agents, leading to obstruction of the hair cuticle, decreased water content, degradation of keratin proteins and other constituents of the hair, or the like. The damaged state of the hair leads to splitting of the hair and breaking of the hair, drying out of the hair, decreased elasticity, etc.

The cosmetic industry has traditionally treated these problems using silicones, fats and oils, amino acids, polyols, etc. However, the benefits of standard conventional treatments have shortcomings in scope of treatment and are not beneficial for a broad range of hair and skin conditions.

The present invention contains water-soluble silk protein, which deposits onto the skin or the natural hair keratin to provide a smooth and durable film to provide added strength for protection against environmental, chemical, and grooming associated damage. Furthermore, cationic polysaccharides, including but not limited to chitosan and its corresponding derivatives, bind to human skin and hair and provide damage control by binding to the amino acids comprising the hair when the hair has been damaged by surfactants, dyeing, and perming. The seed oils present in the emulsions provide a moisture barrier and act as carriers of the nutrients into the pores of the hair and skin.

Botanical extracts contain polyphenols, among other actives, which contribute to a wide range of medicinal qualities such as Anti-inflammatory effect, Anti-cancer effect, Potent DHT inhibitor, stimulant, among others. For example, the bark and roots of *Myrica rubra* contain essential oil, triterpenes (taraxerol, myricadiol), gallic tannins and flavonoids (myricetin and dihyidromyricetin). Among them, myricetin is the standardized compound in the extract which is astringent and stimulant, and has anti-inflammatory and anti-cancer effects.

Botanicals, such as *Myrica rubra* extract, rosehip extract, and green tea extract, contain flavonoids which are naturally occurring phenolic compounds, found in plants, that exhibit a variety of biological activities, including suppression of inflammation, cancer chemoprevention, and protection from vascular disease.

Compounds such as organic anthocyanins and other plant pigments are found in the hibiscus, in addition, relatively large amounts of the oxalic, malic, citric—12% to 17%, and tartaric acids are also found. The herb also contains very appreciable quantities of many water soluble mucilaginous polysaccharides in high proportions to the total volume. These water soluble mucilaginous polysaccharides coat and protect the hair and skin.

Furthermore, the combination of amino acids, polyol, D-ribose, polysaccharide, and fatty acids are expected to increase oxygen uptake of the hair follicle with the result of stimulating the metabolic processes of the hair follicle leading to reparation of damaged follicles. While the cationic polysaccharides and the silk proteins bind to the hair thereby controlling damage to the hair.

Both oil/water (O/W) emulsions and water/oil (W/O) emulsion systems have been prepared. O/W systems are formulated for the treatment of dry skin and hair conditions. W/O based systems are formulated for skin and hair which is excessively dry damaged, and porous, which require higher concentration of follicle-penetrating oils.

EXPERIMENTAL DATA

Water/Oil Preparation for Hair Care and Hair Growth Conditioner
Phase A: Olive oil (5-25%), coconut oil (20-40%), Flaxseed oil (5-25%), jojoba oil (5-25%), Sorbitan olivate (1-9%), Sucrose cocoate (0.05-2%), Behenyl alcohol (1-5%), PCA Glyceryl Oleate (0.1-4%), Illipe butter (0.05-6%).
Phase B: Purified water (5%-20%), Citrus pectin (0.001-0.05%), Chitosan (0.003-0.05%), Sodium chloride (0.003%-0.05%), Citric acid (0.1-1%), Hydrolyzed keratin (0.03%-3%), Silk amino acids (0.1%-0.7%), Sericin (0.03%-3%), Aloe vera (0.005%-1%), Glycerine (5-15%), Potassium sorbate (0.04-2%), D-ribose (0.001%-3%), *Myrica rubra* extract (0.003-5%), Sodium PCA (1%-13%), Kelp (0.01-2%), Panthenol (1-5%), Chitosan succinamide (0.1-5%), Sunflower seed extract (0.003-5%), *Muira Puamah* extract (0.003-5%).
Phase C: vitamin e acetate (0.04%-4%), Natural Fragrance (0.05%-3%), Manuka oil (0.05%-3%).

Oil/Water Preparation for Leave-in Hair Care and Hair Growth Conditioner
Phase A: Cucumber Seed extract (0.1-4%), Purified water (50-90%), Citrus pectin (0.001-0.05%), Chitosan (0.003-0.9%), citric acid (0.1-1%), Sericin (0.03%-3%), aloe vera (0.005%-1%), potassium sorbate (0.04-2%), D-ribose (0.001%-3%), *Myrica rubra* extract (0.003%-5%), Kelp (0.01-3%), Panthenol (1-5%), Sorbitol (1-11%), Chitosan succinamide (0.1-5%), Sunflower seed extract (0.003-5%), *Muira Puama* extract (0.003-5%).
Phase B: Olive oil (5-10%), coconut oil (5-10%), Flaxseed oil (5-10%), jojoba oil (5-10%), Behentrimonium methosulfate (0.05-2%), Behenyl alcohol (0.5-5%), Illipe butter (0.05-6%).
Phase C: vitamin e acetate (0.04%-4%), Natural Fragrance (0.05%-3%), Manuka oil (0.05%-3%).

Oil/Water Preparation for Rinse Out Hair Care and Hair Growth Conditioner for Normal to Dry Hair
Phase A: Honey (1-10%), Purified water (50-90%), Citrus pectin (0.001-0.05%), Chitosan (0.003-0.9%), citric acid (0.1-1%), hydrolyzed keratin (0.03%-5%), silk amino acids (0.1%-0.7%), Sericin (0.03%-3%), aloe vera (0.005%-1%), potassium sorbate (0.04-2%), D-ribose (0.001%-3%),

*Myrica rubra* extract (0.003%-5%), Sunflower seed extract (0.01-3%), Chamomile flower extract (0.01-3%), *Rosmarinus officinalis* extract (0.01-3%), *Arctium lappa* extract (0.01-3%), Quinoa extract (0.01-3%), Panthenol (1-5%), Sorbitol (1-11%), *Muira Puama* extract (0.003-5%).

Phase B: Sweet almond oil (1-10%), Avocado oil (1-10%), Sucrose cocoate (0.1-5%), Behentrimonium methosulfate (0.05-5%), Behenyl alcohol (0.05-5%).

Phase C: vitamin e acetate (0.04%-4%), Natural Fragrance (0.05%-3%), Manuka oil (0.05%-3%).

/Water Preparation for Rinse Out Hair Care and Hair Growth Conditioner for Dry Hair Phase A: Honey (1-10%), Purified water (50-90%), Citrus pectin (0.001-0.05%), Chitosan (0.003-0.9%), citric acid (0.1-1%), hydrolyzed keratin (0.03%-5%), silk amino acids (0.1%-0.7%), Sericin (0.03%-3%), aloe vera (0.005%-1%), potassium sorbate (0.04-2%), D-ribose (0.001%-3%), *Myrica rubra* extract (0.003%-5%), Sunflower seed extract (0.01-3%), Chamomile flower extract (0.01-3%), *Rosmarinus officinalis* extract (0.01-3%), *Arctium lappa* extract (0.01-3%), Quinoa extract (0.01-3%), Panthenol (1-5%), Sorbitol (1-11%), *Muira Puama* extract (0.003-5%), Chitosan succinamide (0.1-5%).

Phase B: Sweet almond oil (1-10%), Avocado oil (1-10%), Sucrose cocoate (0.1-5%), Behentrimonium methosulfate (0.05-5%), Behenyl alcohol (0.05-5%), Illipe butter (0.05-6%).

Phase C: vitamin e acetate (0.04%-4%), Natural Fragrance (0.05%-3%), Manuka oil (0.05%-3%).

Preparation for Hair Care and Hair Growth Shampoo Low Foam

Phase A: Purified water (50-90%), Cocamidopropyl Hydroxysultaine (5-18%), Sodium Cocoyl Glutamate (3-10%), *Yucca schidigera* extract (1-10%), *Saponaria officinalis* (1-10%), Sucrose cocoate (1-10%), Soapwort root extract (1-10%).

Phase B: Camellia oil (1-10%).

Phased C: Honey (1-10%), Citrus pectin (0.001-0.05%), Chitosan (0.003-0.9%), citric acid (0.1-1%), Hydrolyzed keratin (0.03%-5%), silk amino acids (0.1%-0.7%), Sericin (0.03%-3%), potassium sorbate (0.04-2%), Glycerine (5-15%), D-ribose (0.001%-3%), *Myrica rubra* extract (0.003%-5%), Sodium PCA (0.01-5%), Hibiscus flower extract (0.01-3%), Ginger extract (0.01-3%), Green tea extract (0.01-3%), Sandalwood extract (0.01-3%), Rosehip extract (0.01-3%), *Ginkbo biloba* extract (0.01-3%), Mango extract (0.01-3%), Ashwaganda extract (0.01-3%), Kelp (0.01-3%), Allantoin (0.1-5%), Xanthan gum (0.1-3%), Sodium citrate (0.1-2%), *Muira Puama* extract (0.003-5%).

Phase D: vitamin e acetate (0.04%-4%), Eucalyptus oil (0.01%-3%), Sage clary oil (0.01-3%), Natural Fragrance (0.05%-3%)

Preparation for Hair Care and Hair Growth Shampoo No Foam

Phase A: Purified water (50-90), Sucrose cocoate (1-15%).

Phase B: Camellia oil (1-10%).

Phased C: Honey (1-10%), Citrus pectin (0.001-0.05%), Chitosan (0.003-0.9%), citric acid (0.1-1%), Hydrolyzed keratin (0.03%-5%), silk amino acids (0.1%-0.7%), Sericin (0.03%-3%), potassium sorbate (0.04-2%), Glycerine (5-15%), D-ribose (0.001%-3%), *Myrica rubra* extract (0.003%-5%), Sodium PCA (0.01-5%), Hibiscus flower extract (0.01-3%), Ginger extract (0.01-3%), Green tea extract (0.01-3%), Sandalwood extract (0.01-3%), Rosehip extract (0.01-3%), *Ginkbo biloba* extract (0.01-3%), Mango extract (0.01-3%), Ashwaganda extract (0.01-3%), Kelp (0.01-3%), Allantoin (0.1-5%), Xanthan gum (0.1-3%), Sodium citrate (0.1-2%), *Muira Puama* extract (0.003-5%).

Phase D: vitamin e acetate (0.04%-4%), Eucalyptus oil (0.01%-3%), Sage clary oil (0.01-3%), Natural Fragrance (0.05%-3%)

Preparation for Carrier Oil-Free Smoothing Gel

Phase A: Honey (1-10%), Purified water (50-90%), Citrus pectin (0.001-0.05%), Chitosan (0.003-0.9%), citric acid (0.1-1%), hydrolyzed keratin (0.03%-5%), silk amino acids (0.01%-0.7%), Sericin (0.03%-3%), potassium sorbate (0.04-2%), D-ribose (0.001%-3%), *Myrica rubra* extract (0.003%-5%), Sodium PCA (0.1-2%), Collagen amino acids (0.01-4%), Carob extract (0.01-3%), Grapeseed extract (0.01-3%), Grapefruit seed extract (0.01-3%), *Rosmarinus officinalis* extract (0.01-3%), Olive seed extract (0.01-3%), Seaweed codium vermilara extract (0.01-3%), Panthenol (1-5%), Sorbitol (1-11%), Polysorbate 60 (0.03-5%), Xanthan gum (0.02-2%).

Phase B: vitamin e acetate (0.01%-4%), Fragrance (0.05%-3%)

Preparation for Carrier Oil Containing Smoothing Gel

Phase A: Honey (1-10%), Purified water (50-90%), Citrus pectin (0.001-0.05%), Chitosan (0.003-0.9%), citric acid (0.1-1%), hydrolyzed keratin (0.03%-5%), silk amino acids (0.01%-0.7%), Sericin (0.03%-3%), potassium sorbate (0.04-2%), D-ribose (0.001%-3%), *Myrica rubra* extract (0.003%-5%), Sodium PCA (0.1-2%), Collagen amino acids (0.01-4%), Carob extract (0.01-3%), Grapeseed extract (0.01-3%), Grapefruit seed extract (0.01-3%), *Rosmarinus officinalis* extract (0.01-3%), Olive seed extract (0.01-3%), Seaweed codium vermilara extract (0.01-3%), Panthenol (1-5%), Sorbitol (1-11%), Polysorbate 60 (0.03-5%), Xanthan gum (0.02-2%).

Phase B: Plum kernel oil (1%-10%), Behentrimonium methosulfate (0.05-5%), Behenyl alcohol (0.05-5%), PCA Glyceryl Oleate (0.1-4%).

Phase C: vitamin e acetate (0.01%-4%), Fragrance (0.05%-3%)

General Procedure for Preparation of Hair Care and Hair Growth Conditioner and Gels Phase A was prepared in stainless-steel apparatus with agitation at low speed (approx. 200 rpm) and heated to 75 C-80 C. Phase B was prepared similarly with agitation at low speed and heating to 75 C-80 C. Phase A was then agitated at high speed (over 1000 rpm), subsequently Phase B was slowly added to Phase A. High speed agitation was continued for 5 minutes. The mixture was cooled to 45-50 C, then phase C was added to mixture and the mixture was allowed to cool to room temperature with low speed agitation.

General Procedure for Preparation of Hair Care and Hair Growth Shampoo

Phase A was prepared in stainless-steel apparatus with agitation at low speed (approx. 200 rpm) and heated to 75 C-80 C. Phase B followed by Phase C were added with agitation and heating to 75 C-80 C. The mixture was cooled to 45-50 C, then phase D was added to mixture and the mixture was allowed to cool to room temperature with low speed agitation.

General Procedure for Preparation of Hair Care and Hair Growth Smoothing Gel

Phase A was prepared in stainless-steel apparatus with agitation at low speed (approx. 200 rpm) and heated to 75 C-80 C. The mixture was cooled to 45-50 C, then phase B was added to mixture and the mixture was allowed to cool to room temperature with low speed agitation.

Further Applications

The emulsion systems for the W/O are currently composed of, but not limited to suitable monoester of fatty acids derived from olive oil and sorbitol (sorbitan olivate), and monoester of sucrose esters of coconut acids derivatives (sucrose cocoate). Suitable emulsion stabilizer is composed of, but not limited to individual components/or combination of single oleate derivative, PCA glyceryl oleate; propylene glycol ether derivatives of cellulose (hydroxypropyl methylcellulose); and/or long-chain fatty alcohols (behenyl alcohol, cetyl alcohol, stearyl alcohol, or other suitable long-chain fatty alcohols). The W/O emulsifier system may vary within limits. It is preferable to use a combination of nonionic, unsaturated, long-chain fatty acid ester of low hydrophilic/lipophilic balance (HLB) value in combination with a high HLB polyethoxylated fatty acid ester.

These emulsions, which are in the form of creams, oils, gels, have good film-forming properties and give a very satisfactory sensation after they have been applied. Such emulsions can be used as skin care, skin cleansing. When these compositions are skin care products, including but not limited to anti-wrinkle products for improving the appearance of the skin. These can be used as skin care and anti-wrinkle products with the addition of a range of vitamins, including but not limited to vitamin A, B, C sources and derivatives derived thereof (0.05%-5%). Addition of carbohydrates is recommended, preferably, but not limited to the glycosaminoglycan hyaluronic acid (0.01%-2%). Addition of botanical extracts, preferably, but not limited to green tea extracts (0.5%-7%). Addition of exfoliating agents is recommended, preferably, but not limited to avena saliva kernel flour (0.05%-5%).

These emulsions, which are in the form of creams, oils, and gels, based on their ability to promote hair growth, exhibit epidermal penetration properties, and give a very satisfactory sensation after they have been applied. Such emulsions can be used as topical ointments. These compositions may be suitable health care products, including, but not limited topical ointments for the relief of pain. These can be used as topical products with the addition of a range of vitamins, including but not limited to vitamin A, B, C sources and derivatives derived thereof (0.05%-5%). Addition of marine extracts is recommended, preferably, but not limited to kelp (0.05%-5%). Addition of botanical extracts, preferably, but not limited to Ho Shou Wu root extracts (0.005%-3%). Addition of high molecular weight wax is recommended, preferably, but not limited to medical grade lanolin (2%-20%).

The invention claimed is:

1. A topical composition comprising:
   *Myrica rubra* extract in a *Myrica rubra* extract concentration range of approximately 0.003% to 5%;
   Chitosan in a Chitosan concentration range of approximately 0.003% to 0.05%; Sericin in a Sericin concentration range of approximately 0.03% to 3%; Ribose in a Ribose concentration range of approximately 0.001% to 3%; and silk amino acids in a silk amino acid concentration range of approximately 0.1% to 0.7%; wherein the topical composition comprises either an oil/water or a water/oil emulsion.

2. A method for treating hair, the method comprising administering to a patient an amount of the topical composition of claim 1, the amount being effective to treat a denatured protein structure of the hair.

3. A method for treating hair, the method comprising administering to a patient an amount of the topical composition of claim 1, the amount being effective to treat a degradation of at least one of keratin proteins and other constituents of the hair.

4. A method for treating skin, the method comprising administering to a patient an amount of the topical composition of claim 1, the amount being effective to treat an obstruction of a hair cuticle on the skin.

5. A method for treating skin, the method comprising administering to a patient an amount of the topical composition of claim 1, the amount being effective to treat a decreased water content of the skin.

6. The topical composition as in claim 1, further comprising:
   citrus pectin in a citrus pectin concentration range of approximately 0.001% to 0.05%;
   aloe vera in an aloe vera concentration range of approximately 0.005% to 1%;
   panthenol in a panthenol concentration range of approximately 1% to 5%;
   potassium sorbate in a potassium sorbate concentration range of approximately 0.04% to 2%;
   sunflower seed extract in a sunflower seed extract concentration range of approximately 0.003 to 5%;
   *Muira puama* extract in a *Muira puama* concentration range of approximately 0.003% to 5%;
   Vitamin E acetate in a Vitamin E acetate concentration range of approximately 0.04% to 4%;
   at least one oil selected from the group consisting of olive oil in a concentration range of approximately 5 to 25%, flaxseed oil in a concentration range of approximately 5 to 25%, and camellia oil in a concentration range of approximately 1 to 10%; and
   citric acid in a citric acid concentration range of approximately 0.1% to 1%.

7. The topical composition as in claim 6, wherein the sunflower seed extract concentration is approximately 0.01% to 3%.

8. The topical composition as in claim 6, further comprising hydrolyzed keratin in a hydrolyzed keratin concentration range of approximately 0.03% to 5%.

9. The topical composition as in claim 6, further comprising Chitosan succinamide in a Chitosan succinamide concentration range of approximately 0.1% to 5%.

10. The topical composition as in claim 6, further comprising cucumber seed extract in a cucumber seed extract concentration range of approximately 0.1% to 4%.

11. The topical composition as in claim 1, further comprising: citrus pectin in a citrus pectin concentration range of approximately 0.001% to 0.05%.

12. The topical composition as in claim 1, further comprising: aloe vera in an aloe vera concentration range of approximately 0.005% to 1%.

13. The topical composition as in claim 1, further comprising: panthenol in a panthenol concentration range of approximately 1% to 5%.

14. The topical composition as in claim 1, further comprising: potassium sorbate in a potassium sorbate concentration range of approximately 0.04% to 2%.

15. The topical composition as in claim 1, further comprising: sunflower seed extract in a sunflower seed extract concentration range of approximately 0.003 to 5%.

16. The topical composition as in claim 1, further comprising: *Muira puama* extract in a *Muira puama* concentration range of approximately 0.003% to 5%.

17. The topical composition as in claim 1, further comprising: Vitamin E acetate in a Vitamin E acetate concentration range of approximately 0.04% to 4%.

18. The topical composition as in claim 1, further comprising: at least one oil selected from the group consisting of olive oil in a concentration range of approximately 5 to 25%, flaxseed oil in a concentration range of approximately 5 to 25%, and camellia oil in a concentration range of approximately 1 to 10%.

19. The topical composition as in claim 1, further comprising: citric acid in a citric acid concentration range of approximately 0.1% to 1%.

20. A topical composition comprising:
- *Myrica rubra* extract in a *Myrica rubra* extract concentration range of approximately 0.003% to 5%;
- Chitosan in a Chitosan concentration range of approximately 0.003% to 0.05%;
- Sericin in a Sericin concentration range of approximately 0.03% to 3%;
- Ribose in a Ribose concentration range of approximately 0.001% to 3%;
- silk amino acids in a silk amino acid concentration range of approximately 0.1% to 0.7%;
- citrus pectin in a citrus pectin concentration range of approximately 0.001% to 0.05%;
- aloe vera in an aloe vera concentration range of approximately 0.005% to 1%;
- panthenol in a panthenol concentration range of approximately 1% to 5%;
- potassium sorbate in a potassium sorbate concentration range of approximately 0.04% to 2%;
- sunflower seed extract in a sunflower seed extract concentration range of approximately 0.003 to 5%;
- *Muira puama* extract in a *Muira puama* concentration range of approximately 0.003% to 5%;
- Vitamin E acetate in a Vitamin E acetate concentration range of approximately 0.04% to 4%;
- at least one oil selected from the group consisting of olive oil in a concentration range of approximately 5 to 25%, flaxseed oil in a concentration range of approximately 5 to 25%, and camellia oil in a concentration range of approximately 1 to 10% citric acid in a citric acid concentration range of approximately 0.1% to 1%.

* * * * *